(12) United States Patent
Vespasiani

(10) Patent No.: US 8,370,176 B2
(45) Date of Patent: Feb. 5, 2013

(54) METHOD AND SYSTEM FOR DEFINING AND INTERACTIVELY MANAGING A WATCHED DIET

(76) Inventor: Giacomo Vespasiani, San Benedetto del Tronto (IT)

( * ) Notice: Subject to any disclaimer, the term of this patent is extended or adjusted under 35 U.S.C. 154(b) by 159 days.

(21) Appl. No.: 12/742,469

(22) PCT Filed: Nov. 20, 2008

(86) PCT No.: PCT/IB2008/003153
§ 371 (c)(1),
(2), (4) Date: May 12, 2010

(87) PCT Pub. No.: WO2009/066158
PCT Pub. Date: May 28, 2009

(65) Prior Publication Data
US 2010/0256993 A1 Oct. 7, 2010

(30) Foreign Application Priority Data
Nov. 21, 2007 (IT) .............................. BO2007A0767

(51) Int. Cl.
*G06Q 50/00* (2012.01)
(52) U.S. Cl. .......................................... 705/3; 600/300
(58) Field of Classification Search .................. 705/2–3; 600/300
See application file for complete search history.

(56) References Cited

U.S. PATENT DOCUMENTS

| 5,454,721 | A | 10/1995 | Kuch |
| 2003/0040821 | A1 | 2/2003 | Case |
| 2006/0136266 | A1* | 6/2006 | Tarassenko et al. ............. 705/3 |
| 2007/0168228 | A1* | 7/2007 | Lawless ........................... 705/2 |

FOREIGN PATENT DOCUMENTS

| WO | WO2006/067222 A | 6/2006 |
| WO | WO2007/067222 A | 6/2007 |

OTHER PUBLICATIONS

International Search Report, Mar. 19, 2009.

* cited by examiner

*Primary Examiner* — Sind Phongsvirajati
(74) *Attorney, Agent, or Firm* — William J. Sapone; Coleman Sudol Sapone P.C.

(57) ABSTRACT

A method for interactive defining and managing of a controlled diet, prescribed to a patient by a doctor/dietician, includes the asynchronous execution of at least two different operational cycles. A first operational cycle is effected through an interactive terminal and includes a step, in which the foods to be consumed in a given meal are chosen from a first food data base, quantifying the chosen food and assessing the congruity of the choices with what is prescribed and transmitting the data to a central processing unit. A second operational cycle executed by the doctor/dietician on a central processing unit, includes acquiring the data related to the quantities and to the composition of the foods chosen by this patient and comparing this data with the dietary order, and if possible acquiring updated orders and transmitting the updated orders to the patient's interactive terminal.

12 Claims, No Drawings

METHOD AND SYSTEM FOR DEFINING AND INTERACTIVELY MANAGING A WATCHED DIET

BACKGROUND OF THE INVENTION

The present invention relates to the technical field concerning telemedicine applied to the nutrition.

In particular, the invention relates to a method for defining and managing an interactive dietary diary, aimed at helping both a subject who must or is going to follow a specific diet, with the aim of optimizing the diet qualitative and quantitative composition, and the doctor/dietician who plans the diet and follows its effects on the subject. The invention relates also to a system, aimed at carrying out the aforesaid method.

BRIEF DESCRIPTION OF THE PRIOR ART

It is known that a large number of persons need an accurate and continuous nutrition control. This can be due to reasons connected with the person's pursuit of physical wellness or maintenance of an optimal bodyweight. However, a particularly controlled diet is necessary first of all for subjects, who are affected by pathologies requiring the imposition of a severe nutrition discipline, or who only risk such pathologies.

According to the conventionally followed method, the doctor/dietician, after having assessed the psycho-physical situation of the subject (hereinafter called "patient", for sake of simplicity) and the nutrition requirements of the same, gives him/her indications, either verbal or written, about the qualitative and quantitative composition of the diet to be followed. Then, during subsequent check visits, the doctor/dietician checks periodically the obtained results and provides for possible adjustments.

The above described approach, although the simplest and the most immediate, implies a series of problems both for the patient, who follows the diet, and for the doctor, who must control the results thereof. A first problem which limits the effectiveness of any dietary approach lies in the patient's scarce knowledge of the food bromatology composition, and in the difficulty of quantification of the portions taken in.

Another problem, still for the patient, lies in the difficulty of remembering what he actually eats for each meal time after time, in qualitative terms, but especially in quantitative terms. Thus, it is complicated for him to value, even approximately, if he observes the nutritional orders over a medium and long period. Methods for systematic recording of the meals composition on paper or on personal computer can become annoying and difficult to put in practice, specially when the patient is outside; in such cases it can be complicated not only to have a computer at one's disposal, but even to have a note pad in one's pocket, so as to record the composition of one's meal. The patient does not always have the possibility to choose food exactly prescribed in his diet; consequently, he should be able to make comparative valuation of different foods, so as to decide whether the foods among which he can choose are compatible with the doctor's orders.

These and other difficulties of the patient affect also the reliability of the information he can transmit to the doctor and consequently of the correctness of valuation the latter makes in order to decide whether maintain or change the orders.

OBJECTS OF THE INVENTION

One of the objects of the present invention is to propose an organizing instrument for the patient, aimed at simplifying his dietary choices and at increasing his capacity to comply with the doctor's orders, and to give the doctor a series of periodical information, particularly precise and punctual, about the actual diet followed by each patient, wholly independent from the visits frequency.

Another object of the invention is to provide the patient with means for easy and immediate consultation, that help him with the qualitative and quantitative valuation of his meals composition.

A further object of the invention is to provide the patient with means, which simplify his recording operations relative to his real diet, as well as those relative to transmission of the relative data to his doctor.

A still further object of the invention is to provide the doctor with a quick and efficient instrument for acquiring quantitative and qualitative information related to the diet actually followed by each patient, and for periodical updating of the corresponding orders, in a way wholly independent from the frequency of the out-patient visits.

SUMMARY OF THE INVENTION

The above mentioned objects are wholly obtained, according to the contents of the claims, by a method for interactive defining and managing of a controlled diet, ordered to a patient by a doctor/dietician or another operator authorized to the function, that includes the asynchronous execution of at least two operational cycles.

A first operational cycle is effected substantially for each meal consumed by the patient, through an interactive terminal, for example a mobile phone, assigned to the above mentioned patient. The interactive terminal executes a program, which is activated by the patient's command, and which operates on the basis of dietary order made by the doctor/dietician for the patient.

The first operational cycle includes a step, in which the foods to be consumed in a given meal are chosen from a first data base of foods, a step of quantification of the chosen foods and a step of valuation of the congruity of the choices made by the patient with what is contained in the order. The first operational cycle includes also a step, during which data related to the quantities and to the composition of the foods chosen by the patient are put at the disposal on a data transmission line.

A second operational cycle, executed by the doctor/dietician on a central processing unit, includes the steps of acquisition, for each patient, of the data related to the quantities and to the composition of the foods chosen by this patient for each meal, of comparison of these data with the dietary orders for this patient, and possible acquisition of an updating of the orders for the same patient, and of transmission of the orders to the patient's interactive terminal on the data transmission line.

DESCRIPTION OF PREFERRED EMBODIMENTS OF THE INVENTION

The characteristics of the invention, as they will result from the claims, are pointed out in the following detailed description, which illustrates a preferred embodiment of a method for interactive defining and managing of a controlled diet, obtained according to the present invention. Such a diet is usually prescribed to a patient by a doctor/dietician, or another operator authorized to the aforementioned function, after one or more visits and the study of the patient's general situation and of his nutrition requirements. The doctor/dietician is also delegated to control the effects of the prescribed diet by means of periodical direct valuations of the patient.

An embodiment of a system aimed at carrying out the foregoing method is also illustrated.

Such a system, in an illustrative and not exhaustive form, includes a terminal of an interactive user and an application program aimed at being executed in the aforesaid terminal. In the illustrated embodiment, the terminal is advantageously a mobile phone with GPRS functionality, of the type equipped with a permanent memory, non-volatile, with read/write aimed at storing the user's data and programs, and capable of housing and executing—such programs in interactive way, i.e. visualizing on its display the execution options of such programs, accepting the choices set by the user and visualizing afterwards the obtained results. The aforesaid system includes also a user program, operating on the above described mobile phone and organized substantially to fulfill the main functions, which will be described afterwards, besides possible additional functions. The program can be started by the patient at any moment, in known ways and substantially depending on the model of the mobile phone used.

In particular, the user program includes a procedure of interaction with the patient, active immediately on the starting of the program and aimed at allowing the patient to see and to choose various program options, by means of a user interface, likewise depending substantially on the operating system of the mobile phone used. The details related to the design of the aforesaid user interface, as well as the detailed program sequence for obtaining the functions that will be described later, are not related typically to this invention and are means commonly known to those having average skill in the art of, therefore they will not be further discussed.

The system includes also, stored permanently in the non-volatile data areas of the mobile phone, a plurality of information necessary for the actuation of the method for defining and controlling of the diet. A part of such information is organized in a first database, containing information including the bromatological composition, that is the content in terms of classes of nutrients (glucides, lipids, proteins), as well as the total calories of one variety of food, such as to include substantially the whole range of foods that the patient can normally eat.

Another part of the information stored permanently is formed by a second database that contains graphic and numeric explanatory information on different quantities of each food present in the first database. For example, for each food there can be a number of photos of the same food showing growing portions, having known bromatological composition. There can also be information related to the weight and the composition of portions quantified in a not particularly strict form, but nearer to the patient's habits and choice way. For example, as far as solid food is concerned, there can be quantifications expressed each time in terms of "slices", "spoonfuls", etc., while for the liquids there can be quantifications like "glassful", "small glassful", "bottle", etc.

A further permanent data area of the mobile phone is aimed at receiving information related to the dietary orders made by the doctor/dietician for that patient. Such orders will contain data related to the patient's nutritional targets, both in quantitative terms for each meal and for a long period of time and in qualitative terms, i.e. related to the ideal bromatological composition of each meal and to that of the daily diet and, if necessary, of a longer period of time.

The orders are usually structured in accordance with the targets, related both to the calories to be assumed in the whole and to the amounts of glucides, lipids, proteins that the patient must possibly not exceed both in a single meal and in a long period of time. Naturally, for each target the patient is allowed an elastic form of managing of each target. That is, he can decide for example, if the situation requires it, to exceed one or more targets related to the single meal, to make up in subsequent ones.

The targets for the single meal are defined by the doctor/dietician on the basis of different factors, such as the patient's physical structure, his metabolism, physical activity performed daily etc.

The user program includes a quantification procedure, which is activated by the patient by means of the user interface procedure in a food choice step, aimed at giving the user graphic information related to the quantities of each of the aforesaid foods, which the patient has eaten or is going to eat.

Moreover, there is an assessment procedure, aimed at processing the information introduced by the patient and related to the foods that he has eaten or is going to eat, and at giving the patient instructions, in graphic or numeric form, related to the congruity of the chosen foods with the order of the doctor/dietician.

A further remote communication procedure, activated by the patient by means of the user interface, or automatically, depending on the case, is aimed at receiving from doctor/dietician information related to the orders, and at transmitting to the same information related to the composition and to the quantity of food eaten by the patient for each meal, in a manner that will be described in detail later on.

The system includes also a central processing unit, usually situated near the doctor's/dietician's studio and at his disposal, and aimed at running a program that monitors the orders made for all the patients during the observation.

The aforesaid monitoring program includes, besides the normal access and user interface functionalities, a communication procedure for communicating with each user's interactive terminal, with which the patients are equipped, and in which the above mentioned user program is run. In case, in which the interactive terminal is a mobile phone, the central processing unit includes a communication interface for communication with the cellular telephone network, constituted for example by another telephone connected to the processor by standard data transmission line (USB, Bluetooth, etc.).

The monitoring program includes also a storage and visualization procedure, on doctor's/dietician's demand, for storing and displaying the information related to the composition and the quantity of food eaten by each patient, and to the congruity of what has been eaten with the relative orders. It includes also a procedure for acquisition, storage and transmission of updates related to the orders, both in quantitative terms and in terms of composition, to the aforesaid interactive terminals.

The communication line between the central processing unit and the user's terminals of the system is preferably a standard line of the cellular telephone network, having the GPRS functionality. In this connection, the use of the GPRS protocol is advisable, as it allows transmission of data in a rapid and secure way, and in addition it is easy to use. However, the use of such functionality is not necessary for carrying out the present invention, since other data transmission and receipt functionalities can be used, as for example, in a cellular telephone network, the SMS or MMS functionalities.

The method for interactive defining and managing of a controlled diet according to the invention includes asynchronous execution of at least two operational cycles. A first operational cycle is performed periodically by the patient at a close rate, preferably more times a day. Actually, in order to exploit the invention potentiality in optimal way, the patient should activate the above mentioned first operational cycle at the time of each meal, that is each time he is going to eat food.

In such first cycle, the user program, once started, gives the patient a possibility to input the name of food he is going to eat. If the food is contained in the above described first database, the quantification procedure is run to give graphic and numeric information related to the above mentioned food, in terms of bromatological composition depending on the quantity of food the patient is going to eat, as well as in terms of the target of each nutritional parameter of the prescription, stored in the special area of a permanent memory.

Information related to the food in graphic form can be displayed, as far as the quantities are concerned, in terms of reference image of the chosen quantity, taken from the above described second database. Alternatively or additionally, the same quantitative information can be displayed by means of weight in grams of the chosen food, or using non strict measure units, but closer to the daily habits and to the patient's usual choosing way. As already mentioned, such information can be of the type "a slice", "a glassful", "a teaspoonful", etc.

Together with the quantitative information, the quantification procedure displays the bromatological composition of the chosen food, the target fixed by the doctor's/dietician's prescription in terms of calories, glucides, lipids, proteins, and the incidence of the choice made with respect to such target. Such visualization can occur in different known ways, for example, by means of bars calibrated in percentage, which show for each single nutritional parameter, how much of the quantity set by the prescription has already been used, the incidence of the new choice and the distance from the target.

The above mentioned display becomes part of another operational step of the present method that includes an assessment of the congruity of the choices the patient has made or is going to make with what has been set by the prescription. Since the patient has at his disposal, in real time, all the information necessary to quantify the result of his choices in terms of incidence on the prescription, he can understand immediately to what extent his nutritional choices are compatible with the prescription for each single meal and for a long period of time and if the possible deviation from the prescription is acceptable. In this way he can easily make up for possible deviations during subsequent meals.

In a further step of the described method all the data related to the quantity and composition of food chosen by the patient in each single meal, are accessible on the communication line, to which the user's terminal and central processing unit are connected. In particular, such data transmission step can be activated optionally during the first operational cycle, with frequency decided by the patient or as agreed by the latter and the doctor/dietician, by a special procedure, which can be run in the operating program of the user's terminal.

A second operational cycle of the present method is aimed at being carried out in a completely asynchronous way with respect to the above described first cycle, by the doctor/dietician on the central processing unit, by means of the monitoring program installed on the same. In particular, the execution of the aforesaid second cycle can be normally performed at much longer intervals with respect to the frequency of the first cycle, typically once a week.

The above mentioned second operational cycle includes an acquisition step for acquiring, for each patient, data related to the quantity and composition of the food chosen by the patient for each meal. The acquisition takes place after the transmission of such data by the patients and can be performed by acceding to the functionalities of the receiving terminal (for example, a mobile phone of the same type as those supplied to the patients).

After the acquisition of the above mentioned data, a monitoring program procedure is performed, which allows to visualize the data in a form, which is immediately comprehensible to the doctor/dietician, for example in the same quantified graphic form, already described in case of the user's terminal. At the same time, the information related to the latest dietary order for the given patient is visualized. In this way, the doctor/dietician can easily compare what has been prescribed with the patient's real diet, consider its degree of compliance with the prescription and formulate, if necessary and according to his knowledge, changes to the same prescription.

In case, in which the doctor/dietician decides to change the prescription for a given patient, he can activate a procedure for transmitting the new prescription to the user's terminal of this patient. The relative data will be then received by the user program and entered in the permanent data area of his terminal.

As already mentioned, the cellular telephone network with GPRS functionality is particularly indicated for the transmission and receiving of all the data related to the carrying out of the present method. However, as already mentioned, according to the invention, other functionalities, like SMS or MMS can be also used.

The operations of data programming and formatting for the use of all the above described functionalities are highly standardized, within reach of a programmer of average skill, and they do not require innovative activities, therefore they will not be described in a more detailed way.

There are many advantages that the present invention allows to obtain with respect to the known managing methods and systems of the prior art. First of all, the patient is equipped with a complete, versatile and intuitive instrument for updating and monitoring all the data of his controlled diet.

Another advantage results from the help, likewise immediate and intuitive, that the patient receives to calculate his correct food requirements and the correct proportions of the different nutritional factors, depending on his normal activities, or to vary in real time the aforesaid proportions and quantities according to the needs that arrive unexpectedly or to his extemporary food wishes.

A further great advantage that is obtained, results from the fact that the foregoing instrument is supplied to the patient on a support, the mobile phone, to which the patient already got used and which consequently does not represent to him an additional burden or concern. In this way, he will be tendentially moved to exploit its capacities and utility without being annoyed by the necessity to buy an "ad hoc" apparatus and to carry it always with him.

Another advantage of the present method and the related system lies in the help that it gives the doctor/dietician, who can keep the situation of his patients always updated without the necessity to visit them personally, without the necessity to contact them over the phone and without waiting for being contacted by them.

It is understood that what above has been described as a pure, not limiting example. Therefore, possible changes and variants of the invention are to be considered within the protective scope of the present technical solution, as described above and claimed below.

The invention claimed is:

1. A method for interactively managing and refining a diet prescribed to a patient by a diet manager, to promote conformance to the prescribed diet, the method comprising:
providing a portable interactive terminal to said patient;
a central processing unit accessible by said diet manager, said interactive terminal and central processing unit communicating via a communication link;

storing on the interactive terminal:
  i) at least one dietary order received from the diet manager,
  ii) a food database including a range of food products which conform to the prescribed diet, and,
  iii) a food detail database including graphic and numerical food detail information on each food product in the food database, activating a program on the interactive terminal by said patient's command to perform a first operational cycle which is repeated for each meal to be consumed by the patient, said first operational cycle including the steps of:

said patient activating said terminal and choosing from said food database at least one food product to be consumed;

said terminal retrieving and displaying the graphic and numerical food detail information on the chosen food product stored in the food detail database;

said patient selecting a quantity of the chosen food to be consumed from the displayed food detail information;

said program then:

storing the identity of the chosen food and the quantity of the chosen food in the food detail database, hereafter the food detail data, and, comparing the food detail data to the at least one prescribed dietary order to determine conformance with said prescribed dietary order;

storing the determination of conformance in the food detail database, as part of the food detail data;

displaying the determination to the patient, the determination permitting the patient to plan further meals; and, transmitting, on request, the food detail data to the central processing unit;

wherein said diet manager performs a second operational cycle, asynchronously executed in relation to the first operational cycle, the second operational cycle repeated according to a schedule determined by said diet manager, wherein said second operational cycle includes the steps of:

acquiring from said interactive terminal the food detail data and storing the food detail data on the central processing unit;

said diet manager accessing the food detail data, reviewing the accessed food detail data for conformance with the at least one patient dietary order, and determining whether an updated dietary order should be prepared, and if so, preparing an updated dietary order, storing the updated dietary order on said central processing unit; and, transmitting said updated dietary order from the central processing unit to the interactive terminal via said communication link.

2. The method, according to claim 1 wherein said food detail database contains a bromatological composition element for each of said foods in the food database for display in graphic form on the terminal.

3. The method, according to claim 2, wherein said program further performs the step of displaying, for each composition parameter, a target parameter for the meal being composed which conforms to the dietary order.

4. The method, according to claim 1, wherein said step of said terminal retrieving and displaying the graphic and numerical food detail information on the chosen food product stored in the food detail database includes a visual presentation of different quantities of said chosen food.

5. The method, according to claim 4, wherein said visual presentation is in a form of a plurality of photos of said chosen food, each photo presenting a different portion of the chosen food.

6. The method, according to claim 4, wherein said visual presentation is in a numeric form for each different quantity of the chosen food, said numbers indicating a weight for each different quantity of the chosen food portion.

7. The method, according to claim 4, characterized in that said different quantities are a selection of different conventionally used portions of the chosen food product.

8. The method, according to claim 1, wherein the updating of the at least one dietary order is a message sent over a General Packet Radio Service (GPRS) line.

9. A system for interactively managing and refining a diet prescribed to a patient by a diet manager, to promote conformance to the prescribed diet, the system comprising:

a portable interactive terminal for use by the patient and having non-volatile memory areas;

a central processing unit accessible by the diet manager;

a communication link configured to provide communication between the portable interactive terminal and the central processing unit;

the portable interactive terminal having stored therein:

at least one dietary order for said patient received from said diet manager;

a food database including a range of food products which conform to the prescribed diet; and a food detail database including graphic and numerical information detail information on different quantities of each food product contained in said food database;

a program resident in the portable interactive terminal configured to execute on said patient's command to perform a first operational cycle which is repeated for each meal to be consumed by the patient, wherein when the patient chooses a food product or products to be consumed for a given meal from the food database, said program displays the graphic and numerical detail information on the chosen food taken from the food detail database, the patient then quantifying the amount of chosen food product or products based on the data in the food detail database, the quantifying data then stored in the food detail database;

the program then assessing the conformity of the chosen food product or products in relation to the stored at least one dietary order, storing the assessment in the food detail database, and displaying the assessment to the patient;

a program resident on the central processing unit configured to execute on said diet manager's command to perform a second operational cycle which is repeated according to a schedule determined by said diet manager wherein when the diet manager executed the program, said central processing unit communicates with the interactive terminal via the communication link, accesses the food detail database, retrieves the stored data on the food products chosen by the patient, displays the data on the conformity of the chosen food products to the at least one dietary order, the diet manager determining if an update of the at least one diet order is required, and if so, preparing the undated at least one dietary order and transmitting the updated dietary order to the interactive terminal.

10. The system according to claim 9, wherein said interactive terminal is a mobile phone.

11. The system according to claim 9, wherein said mobile phone is equipped with General Packet Radio Service (GPRS) functionality.

12. The system as in claim 9, wherein said communication link is a standard cellular telephone network and said central processing unit is provided with an interface for communication with said cellular telephone network.

* * * * *